United States Patent
Turner

[19]

[11] Patent Number: 5,983,895
[45] Date of Patent: Nov. 16, 1999

[54] TRACHEOSTOMY TUBES AND ASSEMBLIES

[75] Inventor: Mark William Turner, Folkestone, United Kingdom

[73] Assignee: Smiths Industries PLC, London, United Kingdom

[21] Appl. No.: 08/725,032

[22] Filed: Oct. 2, 1996

[30] Foreign Application Priority Data

Oct. 12, 1995 [GB] United Kingdom .................. 9520864

[51] Int. Cl.$^6$ .................................................. A61M 16/00
[52] U.S. Cl. .................... 128/207.14; 128/911; 128/912; 128/200.26
[58] Field of Search .......... 128/200.26, 207.14, 128/911, 912

[56] References Cited

U.S. PATENT DOCUMENTS

| | | |
|---|---|---|
| 2,786,469 | 12/1957 | Cohen . |
| 3,964,488 | 6/1976 | Ring et al. . |
| 4,033,353 | 7/1977 | La Rosa . |
| 4,150,676 | 4/1979 | Jackson . |
| 4,589,410 | 5/1986 | Miller . |
| 4,685,457 | 8/1987 | Donenfeld . |
| 4,817,598 | 4/1989 | LaBombard ........................ 128/207.14 |
| 4,852,565 | 8/1989 | Eisele ................................ 128/207.14 |
| 5,067,496 | 11/1991 | Eisele ................................ 128/207.14 |
| 5,217,008 | 6/1993 | Lindholm ........................... 128/207.14 |
| 5,339,809 | 8/1994 | Beck et al. . |
| 5,458,139 | 10/1995 | Pearl .................................. 128/207.14 |

FOREIGN PATENT DOCUMENTS

| | | |
|---|---|---|
| 0371752A1 | 6/1990 | European Pat. Off. . |
| 1268313 | 5/1968 | Germany . |

*Primary Examiner*—John G. Weiss
*Assistant Examiner*—William J. Deane, Jr.
*Attorney, Agent, or Firm*—Pollock, Vande Sande & Priddy

[57] ABSTRACT

A tracheostomy tube assembly comprises an outer tracheostomy tube and an inner cannula of a flexible material preformed to the shape of the outer tube and smooth on its inside and outside. The outer tube is straight at its patient end and has a short straight machine end with a coupling. The patient and machine ends are separated by a curved intermediate region divided along its length into two sub-regions. The first sub-region closer the machine end has a small radius of curvature; the other sub-region closer to the patient end has a radius of curvature at least three times that of the first sub-region. This shape enables the patient end of the assembly to be aligned with the patient's trachea.

7 Claims, 2 Drawing Sheets

TRACHEOSTOMY TUBES AND ASSEMBLIES

BACKGROUND OF THE INVENTION

This invention relates to tracheostomy tubes and assemblies.

Tracheostomy tubes are used to provide an airway directly to the patient's trachea via a surgically made opening in the neck. The patient end of the tube extends a short distance down the trachea and the machine end projects through the opening so that the patient can breathe freely via the tube. In some cases, the machine end of the tube has a coupling by which the tube can be connected to ventilating equipment. The tracheostomy tube should provide an efficient airway, it should be easy to insert and it should provide a minimum trauma to the patient. Tracheostomy tubes are generally of two different kinds. One kind of tube has a constant curvature along its entire length; the other has a straight section at its patient and machine ends and a curved section of constant radius between the two straight sections.

It is desirable for tracheostomy tubes to have a removable inner cannula or liner extending along the tube, the combination of the tube and inner cannula forming an assembly. The inner cannula is removed and replaced with a new cannula periodically, so as to dispose of any secretions that might have collected on the inside of the cannula. This reduces the risk of the accumulation of bacteria within the assembly and keeps the air passage clear without the need to remove the tube. The wall of inner cannula must be as thin as possible in order to minimize the obstruction to air flow along the assembly but the cannula must be sufficiently stiff to enable it to be inserted in the outer tube. Where the outer tube is curved along its length, the inner cannula can be made with the same curvature and can be inserted freely within the outer tube without deformation. Where the outer tube has straight sections at its ends, the inner cannula must be capable of flexing as it is inserted, so as to follow the shape of the outer tube. In order to ensure that the inner cannula does not buckle as it is inserted, the cannula may be corrugated, although this does reduce the air flow along the assembly. Examples of tracheostomy tubes are described in, for example, GB2251386, U.S. Pat. No. 5,222,487, EP474802, EP507886, GB2224213, GB2213384, GB2205504, GB2084023 and GB2056285.

BRIEF SUMMARY OF THE INVENTION

It is an object of the present invention to provide an improved tracheostomy tube and assembly.

According to one aspect of the present invention there is provided a tracheostomy tube having a straight patient end, a coupling at its machine end and an intermediate region between the patient end and machine end, the intermediate region being curved with a curvature that varies along its length such that the patient end of the tube is substantially aligned with the trachea.

The machine end of the tube may have a short straight region between the intermediate region and the coupling.

According to another aspect of the present invention there is provided a tracheostomy tube having a straight patient end, a short, straight machine end and an intermediate region between the patient end and machine end, the intermediate region being curved with a curvature that varies along its length such that the patient end of the tube is substantially aligned with the trachea.

The intermediate region preferably comprises a first sub-region closer to the machine end of the tube and a second sub-region closer to the patient end of the tube, the first sub-region having a smaller radius of curvature than the second sub-region. The radius of curvature of the second sub-region is preferably at least substantially three times that of the first sub-region. The angle between the patient end and the machine end is preferably substantially 105°.

According to a further aspect of the present invention there is provided a tracheostomy tube assembly comprising a tracheostomy tube according to the above one or other aspect of the invention and an inner cannula of a flexible material inserted within the tracheostomy tube.

The inner cannula is preferably preformed substantially to the shape of the tracheostomy tube and preferably has a smooth surface on its inside and outside.

A tracheostomy tube assembly according to the present invention will now be described, by way of example, with reference to the accompanying drawings.

DETAILED DESCRIPTION OF THE PREFERRED EMBODIMENT

Figure 1:
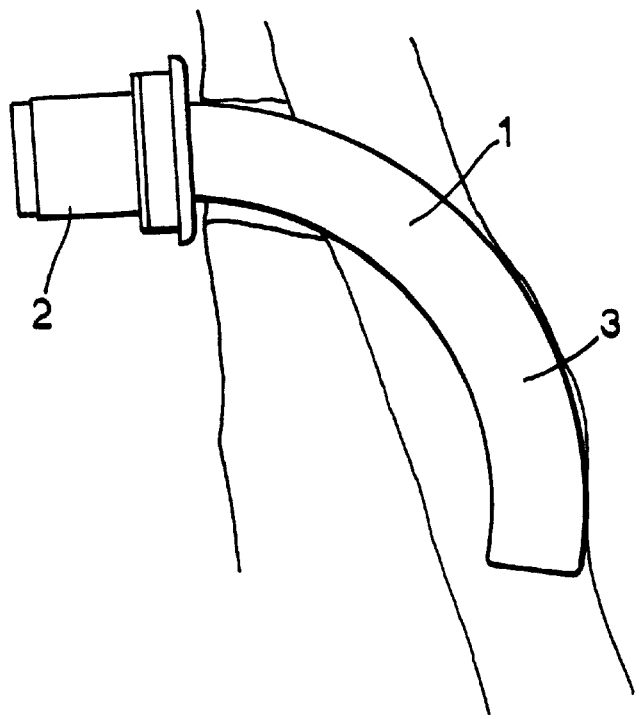
FIG. 1 is a side elevation view of a conventional tube, in use, having a constant curve along its length.

With reference first to FIG. 1, there is shown a conventional tracheostomy tube assembly having an outer tube 1 with a coupling 2 at its machine end and a shaft 3 that is curved along its entire length with a constant radius of curvature. An inner cannula used with the outer tube can have a thin, smooth wall preformed with the same shape as the outer tube and this can be inserted into the outer tube without deforming the inner cannula. The shape of these outer tubes, however, means that the tubes will usually contact the posterior wall of the trachea, with a risk of causing trauma to the lining of the trachea. Also, the patient end of the outer tube will not generally be aligned with the axis of the trachea, so that gas emerging from the patient end of the tube will be directed onto the wall of the trachea.

Figure 2:
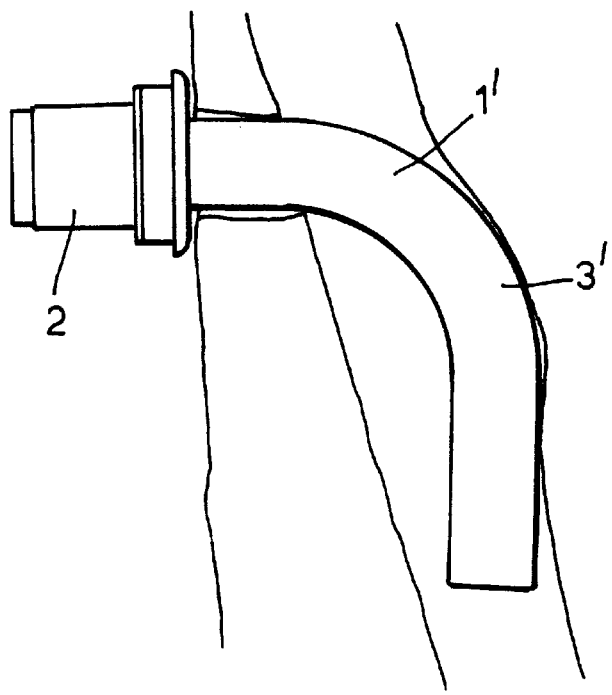
FIG. 2 is a side elevation view of a conventional tube, in use, having straight regions at its patient and machine end.

FIG. 2 shows an alternative assembly with the shaft 3' of an outer tube 1' having straight regions at its machine end and patient end and an intermediate region with a constant radius of curvature, so that the patient and machine ends are inclined at an angle of 90° to one another. This assembly suffers from similar problems to the assembly shown in FIG. 1, in that it is difficult to provide a tube that will not cause trauma to the lining of the trachea. The fact that the outer tube has straight regions leads to further problems, in that the inner cannula must be capable of flexing during insertion. With the shape of outer tube shown in FIG. 2, it is necessary to make the inner cannula corrugated to ensure that it can bend sufficiently without buckling during insertion. This is a disadvantage because it reduces the effective internal diameter of the inner cannula and causes turbulence in gas flow along the cannula.

Figure 3:
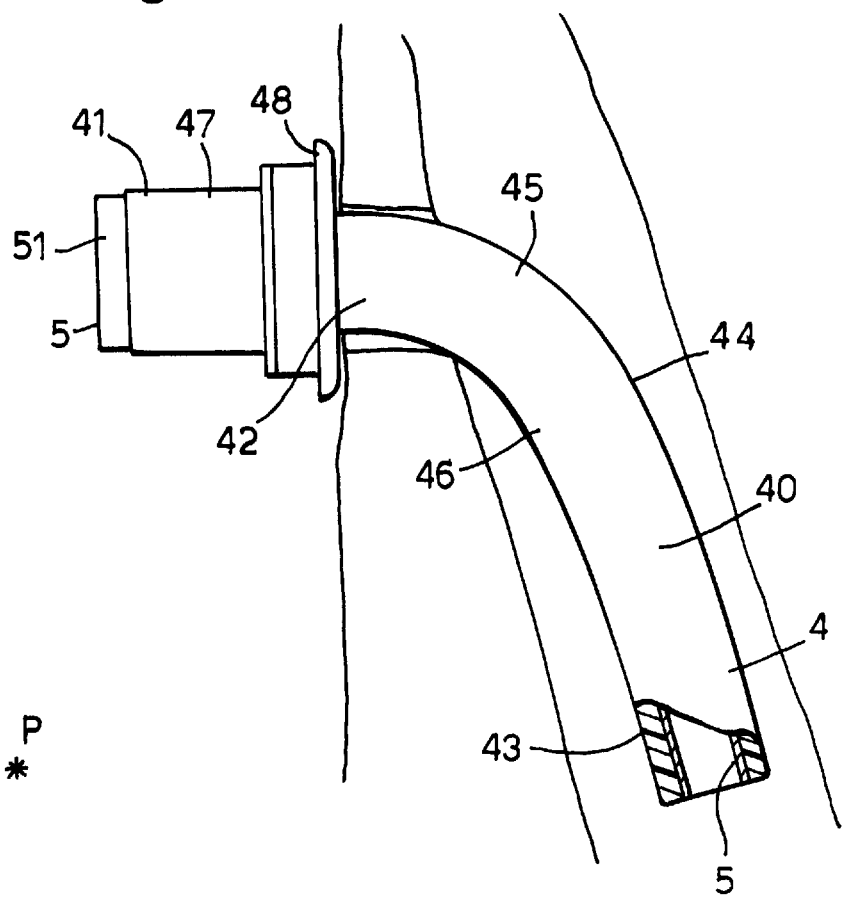
FIG. 3 is a partly sectional side elevation view, in use, of a tracheostomy tube assembly according to the present invention.
Figure 4:
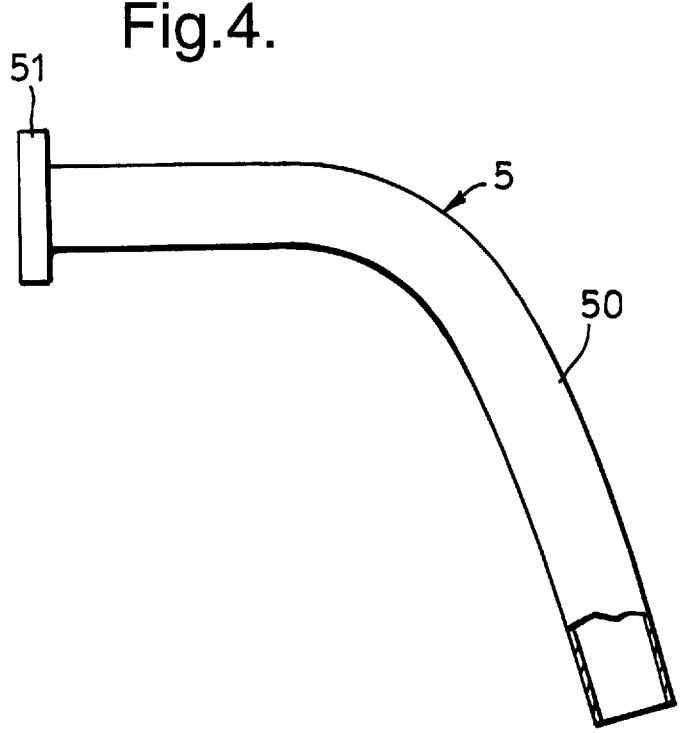
FIG. 4 is a partly sectional side elevation view of an inner cannula for the assembly shown in FIG. 3.

With reference to FIGS. 3 and 4, there is shown a tracheostomy tube assembly according to the present invention comprising an outer tube 4 and an inner cannula or liner 5, which is insertable within, and is removable from, the outer tube. The outer tube 4 comprises a shaft 40 and a coupling 41 at the rear or machine end of the shaft. The shaft 40 is about 66 mm long and is of circular section, having an external diameter of 11.5 mm and an internal diameter of 8 mm. The shaft is made of PVC or a similar plastics material, the wall thickness of the shaft and the nature of the material being such that the shaft is stiff but can be bent, retaining a memory so that it returns to the shape shown in FIG. 3. Along its length, the shaft comprises three regions: a short machine end region 42 about 6 mm long, which is straight and extends coaxially of the coupling 41; a patient end region 43 about 21 mm long, which is straight and extends at an angle of 105° to the machine end region 42; and an intermediate region 44 about 39 mm long, which is curved. The curvature of the intermediate region 44 varies along its length. In particular, the intermediate region 44 is divided along its length into two sub-regions 45 and 46. The sub-region 45 closer to the machine end occupies about one third of the length of the intermediate region 44 and has a relatively tight radius of curvature of 21 mm. The other sub-region 46, closer to the patient end region 43, has a shallower bend, with a radius of curvature of 70 mm, that is, more than three times greater than the sub-region 45. The center of curvature of the patient-end sub-region 46 is at a point P located 46.5 mm below the axis of the coupling 41 and 32 mm to the rear of the machine end of the shaft 40.

The coupling 41 is conventional, having a male tapered external surface 47 and a flange 48 by which the assembly can be secured about the neck of the patient. The coupling 41 is hollow, being open at its machine end and communicating with the bore through the shaft 40.

The inner cannula 5 is shown in FIG. 4 and comprises a shaft 50 and a termination or flange 51 at its machine end. The shaft 50 is the same length as the shaft 40 of the outer tube 4 and its external diameter is the same as the internal diameter of the outer tube. The shaft is pre-formed to the same shape as the outer tube 4 and is made from polythene with a wall thickness of 1 mm, the surface of the shaft being smooth on its inside and outside, that is, the wall is uncorrugated. The termination 51 is of annular shape and has a thicker wall than the shaft 50 so that it is relatively stiff. The termination 51 projects radially outwardly of the shaft so as to limit insertion of the inner cannula 5 by engagement with the machine end of the coupling 41 on the outer tube. The thickness and the nature of the material from which the shaft 50 of the inner cannula is made is such that it can bend to follow the shape of the outer tube 4, as it is inserted, while retaining its circular section, with substantially no buckling, even though the outer tube does not have a constant curvature along its length. The inner cannula 5 need not have exactly the same shape as the outer tube—in some cases, it may be easier to manufacture the inner cannula by making it with a constant curvature along its length. Providing the shape of the inner cannula is approximately the same as that of the outer tube, it can be inserted without buckling.

It has been found that the shape of the outer tube 4 reduces the risk of buckling when the inner cannula 5 is inserted. The sub-region 45 of the outer tube 4, having the tight bend, helps to direct the inner cannula 5 into the more gently bent sub-region 46. It has been found that, by making the sub-region 45 with the tight bend relatively short compared with the sub-region 46 with the shallower bend, there is little risk of buckling.

The assembly is used in the usual way. After performing the tracheostomy, the patient end of the assembly is inserted on an obturator through the surgical opening until the flange 48 is located close to the skin of the patient's neck. The obturator is then removed and a cooperating coupling at one end of tubing connected to ventilation equipment is connected to the coupling 41 on the outer tube. Alternatively, where the patient is breathing spontaneously, the coupling 41 may be left open. The assembly is used normally until the gas passage through the assembly starts to become obstructed by secretions, or until expiry of a predetermined time. The termination 51 on the inner cannula is then gripped, if necessary, after having first uncoupled the ventilation tubing, and the inner cannula 5 is pulled out of the outer tube 4 and disposed of. A new inner cannula is then inserted by pushing in through the coupling 41 and the ventilation tubing is re-coupled to the assembly.

The shape of the outer tube 4 gives it considerable clinical advantages over previous tubes. One advantage arises from the fact that the tip of the patient end of the tube can be located concentrically within the trachea, with the patient end directed coaxially along the trachea. This is a particular advantage with uncuffed tubes where there is nothing on the patient end of the tube to locate it away from the wall of the trachea. Even, however, with cuffed tubes, it has the advantage of ensuring that the pressure exerted by the cuff is distributed equally around the trachea, to avoid local points of high pressure. To achieve the anatomical advantages of the outer tube of the present invention, it is necessary for the tube to have a curvature that is not constant along its length. Although this shape might be expected to require the use of a corrugated inner cannula in order to conform to the shape of the outer tube during insertion without buckling, it has been found that a smooth walled inner cannula can be used satisfactorily. This ensures the least resistance to gas flow along the inner cannula.

What I claim is:

1. A tracheostomy tube assembly comprising a tracheostomy tube and an elongated inner cannula of a flexible material inserted within said tracheostomy tube, wherein said tracheostomy tube includes in its natural state a straight patient end, a machine end, a coupling at said machine end, and an intermediate region between said straight patient end and said machine end, said intermediate region being curved along its entire length, the curvature of said intermediate region varying along its length and the radius of curvature of the intermediate region towards said machine end being smaller than the radius of curvature towards said patient end, such that, in use, said straight patient end of the tube is substantially aligned with the patient's trachea.

2. A tracheostomy tube assembly according to claim 1, wherein said intermediate region comprises a first curved sub-region closer to said machine end of the tube and a second curved sub-region closer to said patient end of the tube, and wherein said first sub-region has a smaller radius of curvature than said second sub-region.

3. A tracheostomy tube assembly according to claim 2, wherein the radius of curvature of said second sub-region is at least substantially three times that of said first sub-region.

4. A tracheostomy tube assembly according to claim 2, wherein said tube has a short straight region between said first curved sub-region and said coupling.

5. A tracheostomy tube assembly according to claim 1, wherein the angle between said straight patient end of the tube and said machine end is substantially 105°.

6. An assembly according to claim 1, wherein said inner cannula is preformed along its length substantially to the shape of said tracheostomy tube.

7. An assembly according to claim 1 or 6, wherein said inner cannula has a smooth surface on its inside and outside.

\* \* \* \* \*